US011752337B2

(12) United States Patent
Gerdes et al.

(10) Patent No.: US 11,752,337 B2
(45) Date of Patent: Sep. 12, 2023

(54) BRAIN REBALANCING THROUGH ACOUSTIC AND ELECTRIC MIRRORING

(71) Applicant: Brain State Technologies, LLC, Scottsdale, AZ (US)

(72) Inventors: Lee Gerdes, Scottsdale, AZ (US); Gillan Smith, Scottsdale, AZ (US); Russell Loucks, River Falls, WI (US); Paul Hastings, Minneapolis, MN (US); Sonya Parker Crittenden, Phoenix, AZ (US)

(73) Assignee: Brain State Technologies, LLC, Scottsdale, AZ (US)

( * ) Notice: Subject to any disclaimer, the term of this patent is extended or adjusted under 35 U.S.C. 154(b) by 553 days.

(21) Appl. No.: 16/981,505

(22) PCT Filed: May 20, 2020

(86) PCT No.: PCT/US2020/033693
§ 371 (c)(1),
(2) Date: Sep. 16, 2020

(87) PCT Pub. No.: WO2020/236866
PCT Pub. Date: Nov. 26, 2020

(65) Prior Publication Data
US 2022/0288391 A1 Sep. 15, 2022

Related U.S. Application Data

(60) Provisional application No. 62/850,806, filed on May 21, 2019.

(51) Int. Cl.
*A61N 1/36* (2006.01)

(52) U.S. Cl.
CPC ..... *A61N 1/36025* (2013.01); *A61N 1/36031* (2017.08); *A61N 1/36034* (2017.08)

(58) Field of Classification Search
CPC ............ A61N 1/36025; A61N 1/36031; A61N 1/36034
See application file for complete search history.

(56) References Cited

U.S. PATENT DOCUMENTS 4,227,516 A * 10/1980 Meland .............. A61N 1/36025
600/26
7,460,903 B2 12/2008 Pineda et al.
(Continued)

FOREIGN PATENT DOCUMENTS

WO 2016209078 A2 12/2016

OTHER PUBLICATIONS

Supplemenatry European Search Report, EP 20 81 0808 (dated Dec. 14, 2022).
(Continued)

*Primary Examiner* — Amanda K Hulbert
*Assistant Examiner* — Philip C Edwards
(74) *Attorney, Agent, or Firm* — Dorf & Nelson LLP; Scott D. Locke

(57) ABSTRACT

Real time mirroring of dominant brain frequencies through the use of two types of stimuli is provided. Through devices and methods that simultaneously look for asymmetries and in real time, one can create real time variable sequences of acoustic and electric stimuli, and then one can effectively and efficiently support the brain to balance its activity between corresponding right and left lobes without one's mindful attention.

18 Claims, 3 Drawing Sheets

(56) References Cited

U.S. PATENT DOCUMENTS

| | | | |
|---|---|---|---|
| 8,239,030 | B1 | 8/2012 | Hagedorn et al. |
| 8,249,699 | B2 | 8/2012 | Gerdes |
| 9,381,352 | B2 | 7/2016 | Yin et al. |
| 9,397,126 | B2 | 7/2016 | Eguchi et al. |
| 9,427,581 | B2 | 8/2016 | Simon et al. |
| 9,433,773 | B2 | 9/2016 | Chao et al. |
| 10,029,067 | B2 | 7/2018 | Gerdes et al. |
| 2006/0136009 | A1* | 6/2006 | Staffel ................ A61N 1/36025 607/46 |
| 2012/0296390 | A1 | 11/2012 | Nakashima et al. |
| 2014/0058189 | A1 | 2/2014 | Stubbeman |
| 2014/0148872 | A1 | 5/2014 | Goldwasser et al. |
| 2015/0342493 | A1 | 12/2015 | Hardt |
| 2016/0129252 | A1 | 5/2016 | Watt et al. |
| 2018/0055402 | A1 | 3/2018 | Izvarina |
| 2018/0154104 | A1* | 6/2018 | Gerdes .................. A61B 5/291 |

OTHER PUBLICATIONS

International Search Report and Written Opinion, PCT/US20/33693 (dated Aug. 26, 2020).

Steffert, Tony (2018). Real-Time Electroencephalogram Sonification for Neurofeedback. The Open University. (Hereinafter referred to as "Steffert").

Destexhe, Alain and Foubert, Luc. A Method to Convert Neural Signals Into Sound Sequences JASA, Jun. 2022 (hereinafter "Destexhe") https://asa.scitation.org/doi/10.1121/10.0011549.

Sanyal, et al Music of Brain and Music on Brain: A Novel EEG Sonification Approach (hereinafter "Sanyal") https://www.ncbi.nlm.nih.gov/pmc/articles/PMC6339862/.

Parvizi, Josef and Chafe, Chris. The Brain in Performance: Converting Brain Waves to Sound and Image 2012 (hereinafter "Parvizi") https://biox.stanford.edu/research/seed-grants/brain-performance-converting-brain-waves-sound-and-image.

Steffert, Tony et al. Prototyping a Method for the Assessment of Real-Time EEG Sonifications, published Jul. 2015 at ICAD 2015 (Hereinafter "Steffen 2"). https://smartech.gatech.edu/handle/1853/54142.

Sonified EEG Could be Useful Triage Tool Neurology Reviews, May 2018 ("Sonified") https://www.mdedge.com/neurology/epilepsyresourcecenter/article/164726/epilepsy-seizures/sonified-eeg-could-be-useful.

Lutters, Bart and Koehler, Peter J. Brainwaves in concert: the 20th century sonification of the electroencephalogram Brain A Journal of Neurology, published Aug. 19, 2016 (hereinafter "Lutters") https://academic.oup.com/brain/article/139/10/2809/2196694.

Baier, Gerold, et al, Live Experiment on Sonification of Human EEG Wein Modern 2008, Nov. 1-5, 2008 (hereinafter Baier) https://www.cit-ec.de/en/ami/live-experiment-sonification-human-eeg.

* cited by examiner

BRAIN REBALANCING THROUGH ACOUSTIC AND ELECTRIC MIRRORING

CROSS-REFERENCE TO RELATED APPLICATIONS

The present application is a national stage application of PCT/US2020/033693 filed May 20, 2020, which claims the benefit of the filing date of U.S. provisional patent application Ser. No. 62/850,806, filed May 21, 2019, the entire disclosures of which are incorporated by reference.

FIELD OF THE INVENTION

The present invention relates to the field of balancing brain waves.

BACKGROUND OF THE INVENTION

Many undesirable physiological, emotional, and behavioral states are correlated with changes in brain activity. These changes in brain activity create electromagnetic energy profiles that can be measured by devices such as electroencephalogram ("EEG") amplifiers and computers. Among the changes in brain activity that are known to be undesirable is an excess asymmetry between activity in the corresponding right and left regions of corresponding lobes of the brain.

One suggestion for restoring symmetry is presented in U.S. Pat. No. 8,249,699, Method of Affecting Balanced Brain Function with Relational Ambient Sound, issued Aug. 21, 2012 to Brain State Technologies, LLC. According to its teaching, due to the ability of the brain to associate sounds with brain waves and then to change its own behavior, a subject is able to develop a relationship between the process of bringing his or her brain to a balanced state and an ambient sound, whereby the ambient sound adds a dimension reminder for the brain to remember moving toward balance. As a result of this relationship, during times of imbalance, one may rebalance that subject's brain functioning.

The teachings of U.S. Pat. No. 8,249,699 illustrate in detail the phenomenon that persons of ordinary skill in the art will recognize as mirroring or echoing, which is distinct from the neuro-feedback teachings of operant conditioning. Strategies that rely on neuro-feedback, including those that rely on EEG biofeedback, have limitations with respect to both precision and speed. Furthermore, they require the mindful attention of the user, which refers to consciously trying to force the brain to do something rather than allowing an experience to simply echo the brain so that the brain can do something on its own terms. Brain echoing is also distinct from traditional transcranial alternating current stimulation (tACS), which relies on external electrical frequencies to change the brain rather than echoing it. Moreover, currently used tACS, by definition, cannot take into account the distinct reflection or echo of the brain in real time.

A more recently developed technology that is directed to echoing of brain activity is described in U.S. Pat. No. 10,029,067, Devices, Systems and Methods for Monitoring Brain Activity for Enabling Brain to Rebalance, issued Jul. 24, 2018 to Brain State Technologies, LLC. In that disclosure, persons of ordinary skill in the art are taught how to combine dynamic monitoring of brain activity and mirroring in real time through sound.

Despite the advances in mirroring technology, there remains a need for new and nonobvious technologies and methods for using mirroring or echoing to balance brain activity without requiring the mindful attention of the user. Various embodiments of the present invention are directed to this need.

SUMMARY OF THE INVENTION

Various embodiments of the present invention provide technologies and methods for balancing bi-hemispheric regions of the brain. In these embodiments, pairs of channels are used to measure brain electromagnetic energy by detecting changes in electric potentials. The measurements are translated from analog to digital and used to calculate brain rhythms. These brain rhythms are analyzed in order to determine when there are threshold asymmetries between corresponding lobes of the brain of a user. When asymmetries are observed, one may use the data to reduce or eradicate the asymmetry through the combination of two types of stimuli. Through the use of the technologies of the present invention, a user's brain may be able to rebalance itself without requiring the attention or volition of the user of the invention or establishing a frequency from outside the dominant frequency that the brain itself is creating at the moment of rebalancing.

According to a first embodiment, the present invention provides a method for decreasing brain asymmetry comprising: (a) simultaneously measuring electromagnetic activity of a user's brain through a set of channels, wherein the set of channels comprises (i) a first pair of corresponding lobe channels, wherein the first pair of corresponding lobe channels is comprised of a right first lobe channel and a left first lobe channel, and (ii) a second pair of corresponding lobe channels, wherein the second pair of corresponding lobe channels is comprised of a right second lobe channel and a left second lobe channel, wherein each channel is configured to measure electromagnetic energy in a region of a brain of a user and to generate a measurement of electromagnetic energy and wherein the first pair of corresponding lobe channels is configured to measure electromagnetic energy from corresponding left-right regions of a first lobe and the second pair of corresponding lobe channels is configured to measure electromagnetic energy from corresponding left-right regions of a second lobe, wherein the first lobe is not the same as the second lobe; (b) determining whether there is a threshold difference in energy between energies measured for any single frequency or for any one or more ranges of frequencies as measured between each channel of each pair of corresponding lobe channels; (c) when there is a determination of a threshold difference in energy, (i) activating a first correlation algorithm, wherein for each of a first plurality of frequencies from a set of dominant middle range brain wave frequencies from a lobe for which there has been a determination of a threshold difference in energy, the first correlation algorithm identifies an acoustic stimulus, and (ii) activating a second correlation algorithm, wherein for each of a second plurality of frequencies from the set of dominant middle range brain wave frequencies from the lobe for which there has been a determination of a threshold difference in energy, intermittently the second correlation algorithm identifies an electric stimulus, wherein the second plurality of frequencies is a subset of the first plurality of frequencies; (d) creating a variable sequence of acoustic stimuli by combining each acoustic stimulus identified in (c)(i) and playing said variable sequence of acoustic stimuli through a sound output device; and (e) delivering to the user each electric stimulus identified in (c)(ii), wherein when each electric stimulus is delivered to the user, an acoustic stimulus that correlates with the same dominant middle range brain wave frequency is simultaneously delivered.

According to a second embodiment, the present invention provides a method for changing brain activity comprising: (a) simultaneously measuring electromagnetic activity of a user's brain through a set of channels, wherein the set of channels comprises (i) a first pair of channels, wherein the first pair of channels is comprised of a right first lobe channel and a right second lobe channel, wherein the right first lobe channel is configured to measure electromagnetic energy in a first lobe in a first hemisphere of a brain of a user and the right second lobe channel is configured to measure electromagnetic energy in a second lobe in the first hemisphere of the brain of the user, and (ii) a second pair of channels, wherein the second pair of channels is comprised of a left first lobe channel and a left second lobe channel, wherein the left first lobe channel is configured to measure electromagnetic energy in the first lobe in a second hemisphere of a brain of a user and the right second lobe channel is configured to measure electromagnetic energy in the second lobe in the second hemisphere of the brain of the user, wherein each channel is configured to generate a measurement of electromagnetic energy, wherein the first hemisphere is not the same as the second hemisphere; (b) determining whether there is a threshold difference in energy between energies measured for any single frequency or for any one or more ranges of frequencies as measured between each channel of each pair of channels; (c) when there is a determination of a threshold difference in energy, (i) activating a first correlation algorithm, wherein for each of a first plurality of frequencies from a set of dominant middle range brain wave frequencies from a hemisphere for which there has been a determination of a threshold difference in energy, the first correlation algorithm identifies an acoustic stimulus, and (ii) activating a second correlation algorithm, wherein for each of a second plurality of frequencies from the set of dominant middle range brain wave frequencies from the hemisphere for which there has been a determination of a threshold difference in energy, intermittently the second correlation algorithm identifies an electric stimulus, wherein the second plurality of frequencies is a subset of the first plurality of frequencies; (d) creating a variable sequence of acoustic stimuli by combining each acoustic stimulus identified in (c)(i) and playing said variable sequence of acoustic stimuli through a sound output device; and (e) delivering to the user each electric stimulus identified in (c)(ii), wherein when each electric stimulus is delivered to the user, an acoustic stimulus that correlates with the same dominant middle range brain wave frequency is simultaneously delivered.

According to a third embodiment, the present invention provides a system for decreasing asymmetry of brain activity, wherein said system comprises: (a) a device, wherein the device comprises a set of channels, wherein the set of channels comprises (i) a first pair of corresponding lobe channels, wherein the first pair of corresponding lobe channels is comprised of a right first lobe channel and a left first lobe channel, and (ii) a second pair of corresponding lobe channels, wherein the second pair of corresponding lobe channels is comprised of a right second lobe channel and a left second lobe channel, wherein each channel comprises at least one sensor and is configured to measure electromagnetic energy in a region of a brain of a user and to generate a measurement of electromagnetic energy, wherein the channels are configured to measure said electromagnetic energy simultaneously and the first pair of corresponding lobe channels is configured to measure electromagnetic energy from a first lobe and the second pair of corresponding lobe channels is configured to measure electromagnetic energy from a second lobe, wherein the first lobe is not the same as the second lobe; (b) an asymmetry determination computer program product, wherein the asymmetry determination computer program product is capable of determining whether a threshold difference in energy exists between energies measured for any single frequency or for any one or more ranges of frequencies as measured between each channel of each pair of corresponding lobe channels; (c) a central processing unit, wherein the central processing unit is configured to receive said measurements of electromagnetic activity from the device and to execute the asymmetry determination computer program product; (d) an acoustic delivery device, wherein the acoustic delivery device is capable of delivering a variable sequence of acoustic stimuli; and (e) an electric stimulus delivery device, wherein the electric stimulus delivery device is configured to deliver microvolt transcranial alternating current stimulation to a user's head. In some embodiments, the device is capable of delivering a continuous variable sequence of acoustic stimuli and an intermittent set of electric stimuli.

According to a fourth embodiment, the present invention provides a system for changing brain activity, wherein said system comprises: (a) a detection device, wherein the detection device comprises a set of channels, wherein the set of channels comprises (i) a first pair of channels, wherein the first pair of channels is comprised of a right first lobe channel and a right second lobe channel, wherein the right first lobe channel is configured to measure electromagnetic energy in a first lobe in a first hemisphere of a brain of a user and the right second lobe channel is configured to measure electromagnetic energy in a second lobe in the first hemisphere of the brain of the user, and (ii) a second pair of channels, wherein the second pair of channels is comprised of a left first lobe channel and a left second lobe channel, wherein the left first lobe channel is configured to measure electromagnetic energy in the first lobe in a second hemisphere of a brain of a user and the right second lobe channel is configured to measure electromagnetic energy in the second lobe in the second hemisphere of the brain of the user, wherein each channel is configured to generate a measurement of electromagnetic energy, wherein the first hemisphere is not the same as the second hemisphere; an asymmetry determination computer program product, wherein the asymmetry determination computer program product is capable of determining whether a threshold difference in energy exists between energies measured for any single frequency or for any one or more ranges of frequencies as measured between each channel of each pair of lobe channels; (c) a central processing unit, wherein the central processing unit is configured to receive said measurements of electromagnetic activity from the device and to execute the asymmetry determination computer program product; (d) an acoustic stimulus delivery device, wherein the acoustic stimulus delivery device is capable of delivering a variable sequence of acoustic stimuli; and (e) an electric stimulus delivery device, wherein the electric stimulus delivery device is configured to deliver microvolt transcranial alternating current stimulation to a user's head.

Throughout this disclosure, systems and methods are described in terms of measuring specific frequencies or ranges or subranges of frequencies. In some embodiments, the invention is described with respect to three subranges or eleven subranges; however, the technologies of the present invention may be used to obtain finer resolution of brain activity and for example, be divided into 3-48 subranges, e.g., 11 subranges or 48 subranges with each subrange corresponding to different sets of frequencies. By using a larger number of subranges and thus narrower subranges, one may be able to obtain a greater understanding of the characteristics of asymmetries when present and to mirror brain activity more efficiently.

Various embodiments of the present invention may be used to restore (or to allow the brain itself to restore or to move toward restoration of) brain balance. According to the present invention, restoration, or decreasing of asymmetry, may be through a combination of real-time mirroring of brain activity through acoustic stimuli and electric stimuli. Systems and methods for detecting brain asymmetry and using acoustic stimuli to move toward brain balance by mirroring through sound are provided in U.S. Pat. No. 10,029,067, the entire disclosure of which is incorporated herein by reference.

Thus, through certain embodiments, the technologies disclosed herein support the brain to recover more optimal oscillatory dynamics with respect to both relative symmetrical activity between the hemispheres and proportionation of energy along the brain electrical activity frequency spectrum. These embodiments may make use of improved support of closed-loop neurotechnology.

BRIEF DESCRIPTION OF THE FIGURES

The systems, methods, and devices disclosed herein and the following detailed descriptions of certain embodiments thereof may be understood by reference to the following figures. Elements in the figures are presented for illustrative purposes, and they are not necessarily drawn to scale.

DETAILED DESCRIPTION

Figure 1:
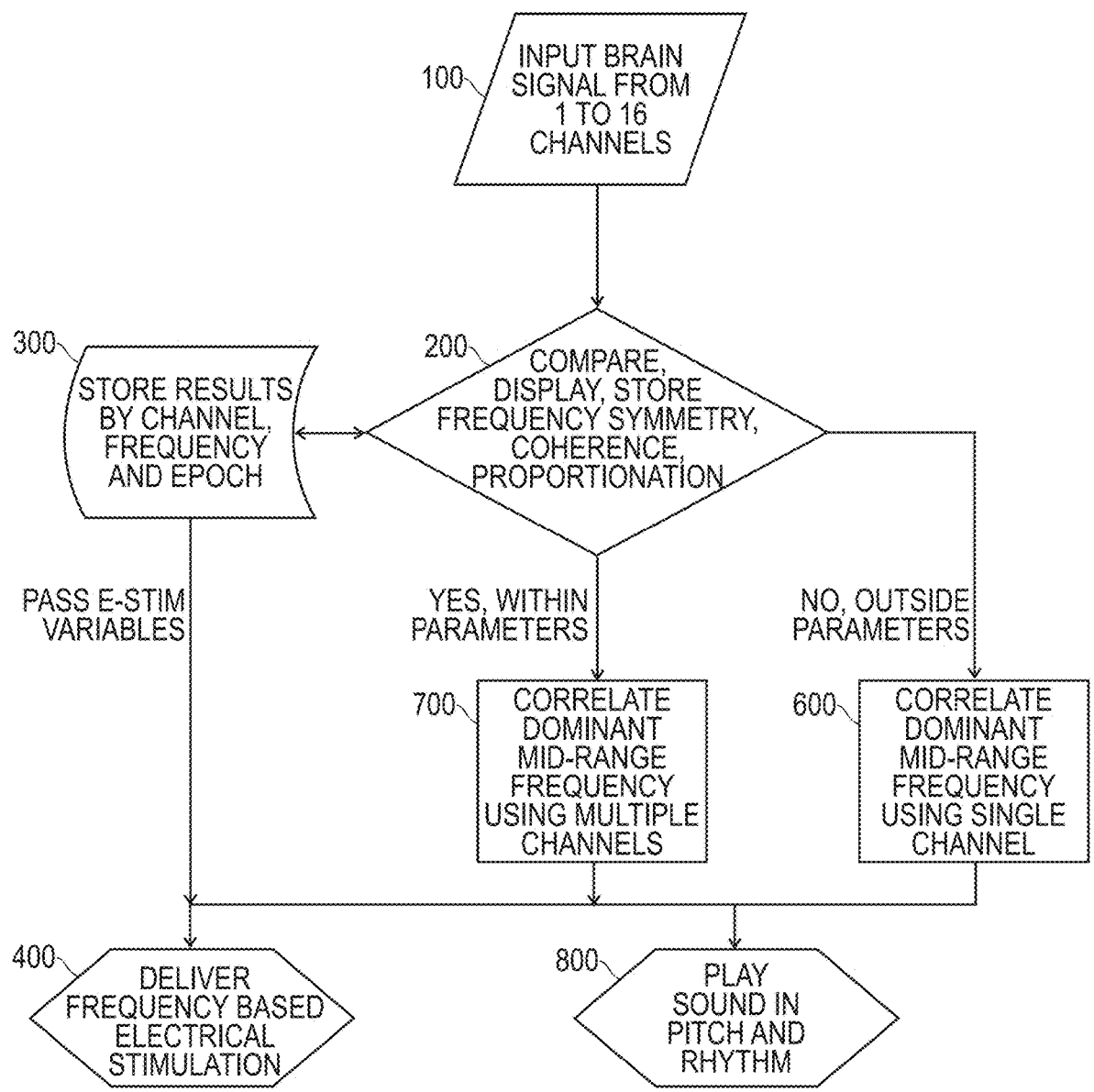
FIG. 1 is a flowchart that depicts steps of rebalancing brain activity according to various methods of the present invention.

The present invention will now be described in detail by describing various illustrative, non-limiting embodiments thereof with reference to the accompanying figures. The invention may, however, be embodied in many different forms and should not be construed as being limited to the illustrative embodiments set forth herein. Rather, the embodiments are provided so that this disclosure will be thorough and will fully convey the concept of the invention to those skilled in the art. Furthermore, headings are provided for the convenience of the reader and are not intended to be and should not be construed as limiting any of the embodiments described herein.

Systems for Decreasing Asymmetry

In one embodiment, the present invention provides a system for decreasing asymmetry of brain activity that comprises: (a) a brain detection functionality, e.g., one or more channels of sensors, optionally contained in a housing; (b) an asymmetry determination computer program product; (c) a central processing unit; (d) an acoustic stimuli delivery functionality, which may, for example, comprise speakers; and (e) an electric stimuli delivery functionality, which e.g., may be in the form of one or more sensors that are optionally the same as or different from the sensors that impart the brain detection functionality.

In some embodiments, one or more components is contained in a housing and distributed symmetrically on the right and left sides of the housing. A distribution is considered to be symmetric between the right side or half and the left side or half if the gross distribution is the same between the right half and the left half, regardless of whether there is any small device or structure in only one half, for example, one or more of a transmitter or receiver or computer chip, or there are components on both halves but they are oriented differently, e.g., turned any number of degrees relative to the corresponding component on the other half, and/or they are located a few millimeters away from the exact mirror location of the corresponding component on the other half of the device. In one embodiment, the system comprises as an amplifier and set of read/write sensors, with the sensors being placed on the scalp at various locations aligning to the 10-20 system. Each of the components of the system is operably coupled to one or more other components so as to allow each component to perform its intended function.

Brain Activity Detection

The brain activity detection functionality may be in the form of a collection of channels that may, for example, be housed or associated with a headband, a hat, a visor, or a helmet and contains a collection of sensors. Optionally, the sensors of the system include or are associated with conductive paste that facilitates association between the sensors and the surface area of the scalp. In addition to any conductive paste that is present, when there is a housing, the housing may comprise a shell for one or more other elements or pieces of hardware, and the shell may have an outer surface that is rigid, e.g., plastic or soft, e.g., mesh or a combination thereof.

The channels are the structures that are configured to detect brain activity, and they may be arranged in pairs of corresponding lobe channels via cabled sensors. The phrase "corresponding lobe channels" refers to channels that are located on opposite sides of the device, i.e., right and left sides, preferably at or close to mirror image locations of each other and in the same or similar orientations, and thus, may be referred to as being located in "corresponding left-right regions" of a lobe.

For illustrative purposes, the brain activity detection functionality may be implemented by four channels that are arranged to collect data (and as discussed more below, in some embodiments also to deliver electric stimulation) from two sets of corresponding lobes, e.g., the left frontal lobe, the right frontal lobe, the left temporal lobe and the right temporal lobe. As persons of ordinary skill in the art will recognize, the device can exist with different numbers of channels for each lobe and multiple pairs of channels for different lobes. For example, 1, 2, 3, 4, 5, 6, 7, 8, 9, 10 or more pairs of channels may be present for each lobe. The number of pairs of channels may be different or the same for different corresponding lobes, and the number of sets of corresponding lobes may be two, three, or four, e.g., frontal and temporal; frontal and parietal; frontal and occipital; parietal and occipital; parietal and temporal; occipital and temporal; frontal, parietal and occipital; frontal, parietal and temporal; frontal, occipital and temporal; parietal, occipital and temporal; and frontal, parietal, occipital and temporal.

As used herein, the phrase "frontal lobe" includes the frontal lobe itself and the frontal pole lobes.

Each channel comprises at least one sensor and is configured to measure electromagnetic energy. The detection functionality of these sensors is configured to detect changes in electric potential and may be able to generate a measurement of electromagnetic energy. Accordingly, the sensors may comprise electrodes, and for each channel of data to be read, there may be one or more electrodes. The electrodes may form or be part of electric read/write sensors that sit against the skin. Thus, within the system, each electrode may be a brain rhythm read device for a particular channel and/or a brain alternating current device for a particular channel.

Preferably, the channels are configured to measure electromagnetic energy simultaneously. Optionally, in addition to EEG sensors, there are EEG amplifiers. Each channel also comprises one or more circuits to transmit data directly or indirectly through hardware wires and/or circuits and/or wirelessly to a common location on the device. The common location may, for example, be a central location, i.e., at or along a line of symmetry of the device (near the top, the base or in between) or the common location may be at a location that is not central.

In some embodiments, the right first lobe channel sensors are positioned to measure electromagnetic energy from the right frontal lobe, the left first lobe channel sensors are positioned to measure electromagnetic energy from the left frontal lobe, the right second lobe channel sensors are positioned to measure electromagnetic energy from the right temporal lobe, and the left second lobe channel sensors are positioned to measure electromagnetic energy from the left temporal lobe. In other embodiments, the right first lobe channel sensors are positioned to measure electromagnetic energy from the right temporal lobe, the left first lobe channel sensors are positioned to measure electromagnetic energy from the left temporal lobe, the right second lobe channel sensors are positioned to measure electromagnetic energy from the right frontal lobe, and the left second lobe channel sensors are positioned to measure electromagnetic energy from the left frontal lobe.

Figure 3:
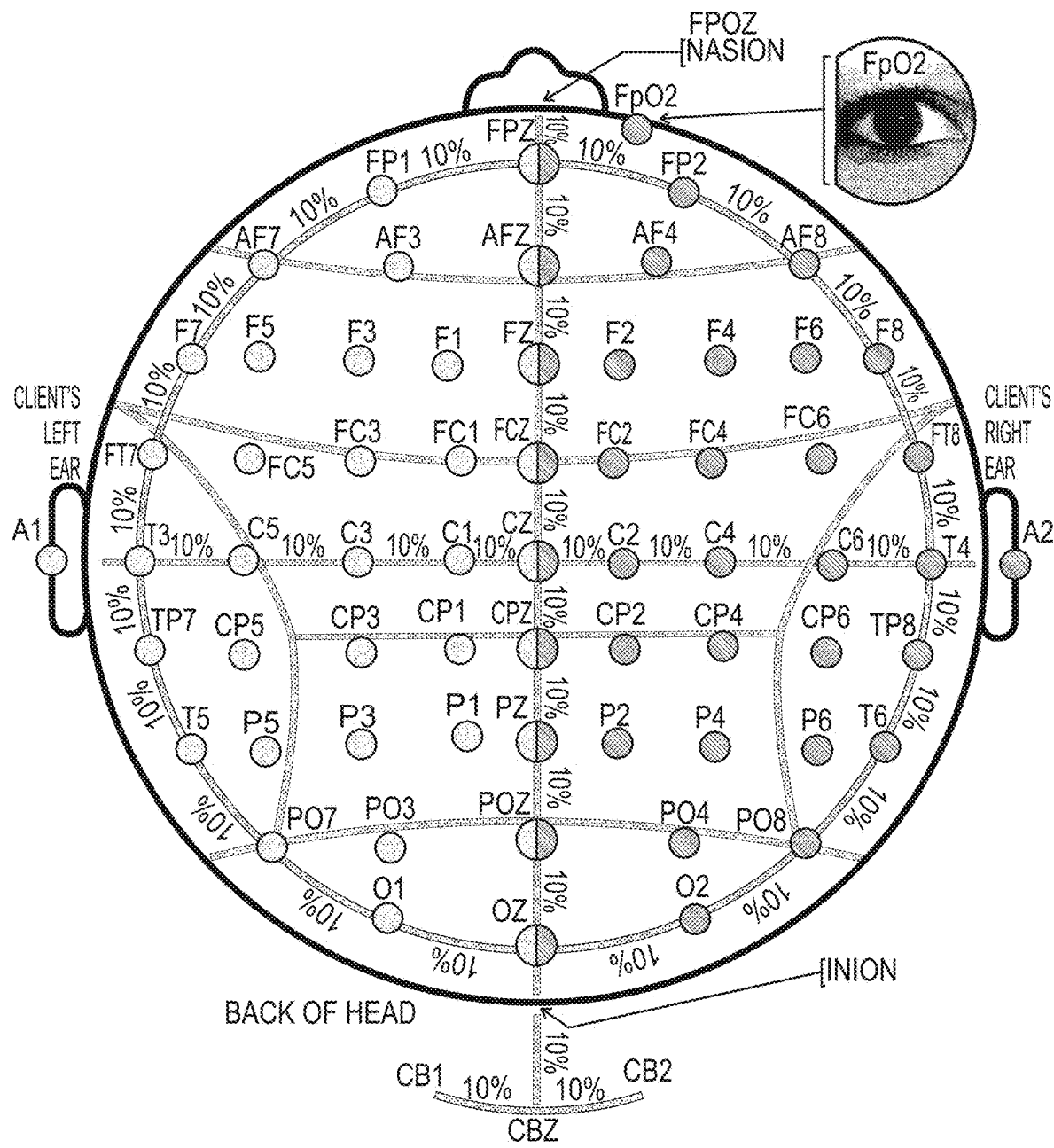
FIG. 3 is a representation of examples of the location of sensors in a system of the present invention. Locations are identified according to the International Standard 10-20 System of EEG placement (the "10-20 system"), and in some embodiments are on CB1/2 (cerebellum left and right).

In addition to the pairs of lobe channels, there may be one or a pair of reference sensors. When there is a pair of reference sensors, each sensor may, for example, be positioned so that when the system is in use, there is a reference sensor at or near each of the user's ears. When there is only one reference sensor and the device is in use, it may be located at or near either the left ear or the right ear or other location of the 10-20 system as shown in FIG. 3. In some embodiments, the system is configured such that it can dynamically switch which sensors are used as reference sensors. In these embodiments, one or more channels may be configured to serve as a reference sensor and there may or may not be separate reference sensors located at or near one or both ears. The dynamic switching may, for example, occur at preprogrammed regular or irregular time intervals.

Stimuli Delivery

The system also contains components that allow for delivery of acoustic stimuli and electric stimuli. These elements provide the means by which to echo brain activity through sound and electric stimuli, respectively. Accordingly, through appropriate instrumentalities, the system is capable of mirroring the middle of ranges brain frequencies through continuous varying sound and intermittent microvolt alternating current. When delivering the intermittent microvolt alternating current, in some embodiments, it is in the form of tACS at the exact same frequency that was dominant in the sub-second of time being investigated and that is mirrored through sound.

The acoustic stimuli may, for example, be delivered through at least one sound output device, e.g., a speaker, and in the form of a variable sequence of acoustic stimuli, which may vary with respect to pitch and/or timing. A "variable sequence of acoustic stimuli" (which also may be referred to as a "varying sequence of acoustic stimuli") is a sequence of sounds that change over time, e.g., musical notes that are played in sequence. In some embodiments, a plurality or each of the sounds has the same duration or different durations and the same or different pitches. In some embodiments, the sounds may, for example, be selected from a scale. As persons of ordinary skill in the art will recognize, a scale is the set of notations that have been accredited by human experience. Thus, in some embodiments, the variable sequences of acoustic stimuli are not based on exact frequencies but instead are based on a relationship between frequencies, or based on the scale of a brain. Although variable, it is not random and any given sequence may be unique.

The electric stimuli may be delivered through electrodes. In some embodiments, the same sensors that can detect brain activity can deliver electric stimuli via an incorporated electrode in the same device head. When delivering electric stimulation, the tACS current flows from the active stimulating sensor(s) to the active ground on the scalp to echo the brain and enhance appropriate symmetry. In some embodiments, the sensors are single (side-by-side) with one reading and one writing (writing=e-stimulating or an echo of the dominant brain frequency in a middle range of that location). In other embodiments, the sensors are combined with both a reading and writing or stimulating component in the same sensor. Additionally there may be one or two reference sensors (e.g., two reference sensors—one on each ear, which are averaged together to equalize any ambient distortion in the room) and there may be many ground sensors although only one ground sensor is used at a time.

Preferably, the electric stimuli are delivered intermittently. Thus, there are periods of time between delivery of electric stimuli in which no electric stimuli are delivered. The electric stimuli may be delivered at irregular or regular intervals (and thus, if at regular intervals, be delivered periodically or cyclically) and for the same or different durations. The intermittent delivery of electric stimuli may be in contrast to the acoustic stimuli, which in some embodiments, is continuous. The intermittent electric stimuli are based on a subset of the real time dominant middle range frequencies that the acoustic stimuli are based. For example, electric stimuli may be administered for 450 to 1500 milliseconds or 600 to 1200 milliseconds in duration. These stimuli may be administered every 1 second to 5 minutes or 15 seconds to 3 minutes or 15 second to 1 minute or 15 second to 30 seconds. The amplitude of the current may, for example, be 5 microvolts to 550 microvolts tACS or 100 microvolts to 200 microvolts tACS. The variable sequence of acoustic and alternating current stimuli are executed in real time while the channels continue to monitor for asymmetries and in some embodiments.

In some embodiments, the electric stimuli is described by one, two, or three of the following variables: (1) interval, which describes how often the electric stimulus may be additionally introduced, e.g., 500 ms (milliseconds) to 60,000 ms on the high with 500 ms resolution; (2) duration, which describes how long the electric stimulus will be given for that dominant frequency trigger, e.g., 450 ms to 5000 ms with 50 ms resolution; and (3) amplitude, e.g., 5 uV (micro volts) to 550 uV with 5 uV resolution.

Ground Electrodes

In addition to the pairs of lobe channels, and sensors, there may be one or a more ground electrodes placed on the scalp. Only one ground electrode will be active for each exercise. The ground electrode determines the path of microvolt alternating current stimulation along the scalp. When there are multiple ground se electrodes attached to the scalp, each electrode may, for example, be positioned within the device so that when the device is in use, there is only one ground electrode that is active. When there is only one active ground electrode and the device is in use, it may be located at or near any location of the 10-20 system as shown in FIG. 3. In some embodiments, the system is configured such that it can dynamically switch which ground electrode is to be used as the active ground electrode. The dynamic switching may, for example, occur at preprogrammed regular or irregular time intervals.

Sound Output Devices

For delivery of acoustic stimuli, systems of the present invention may contain sound output devices, e.g., one or more speakers. In some embodiments the at least one speaker is a set of two speakers, e.g., a left speaker and a right speaker. These speakers may, for example, be located in earbuds or configured as the earpieces of headphones.

In one embodiment the at least one speaker comprises a right speaker and a left speaker and the right speaker is configured to be situated at or near the right ear of the user and the left speaker is configured to be situated at or near the left ear of the user when the device is in use. The set of speakers contains or is operably coupled to elements that contain the requisite hardware and connections in order to receive digital data that corresponds to a variable sequence of acoustic stimuli, and to convert the data into sound to play the variable sequence of acoustic stimuli.

Asymmetry Determination Computer Program

The asymmetry determination computer program product comprises an algorithm that determines whether the difference in brain activity in corresponding lobes is at an undesirable level. This undesirable level may be referred to herein as a threshold or material difference in energy between the lobes. The asymmetry determination computer program product may be stored in a tangible medium or stored in or accessed through the cloud or a network. When applied, the asymmetry determination computer program product determines whether during one or more time periods there is a threshold difference in energy between: (1) energy measured within any one frequency or one or more of a first subranges of frequencies, a second subrange of frequencies, a third subrange of frequencies or any combination of subranges of frequencies, e.g., 11 or 48 subranges of frequencies from a right lobe channel; and (2) energy measured within a corresponding single frequency or one or more subranges of a corresponding left lobe channel, wherein when there are three subranges, the second subrange consists of frequencies greater than the frequencies in the first subrange, and the second subrange consists of frequencies smaller than the frequencies in the third subrange.

The asymmetry determination computer program product is configured to determine whether there is a threshold difference in energy by comparing a calculated energy of the individual frequency or the frequencies within each subrange from the right first lobe channel with a calculated energy of the same frequency or frequencies within each subrange from the left first lobe channel over a plurality of predetermined time periods, and simultaneously comparing a calculated energy of the frequencies within each subrange from the right second lobe channel with a calculated energy of the single frequency or frequencies within each subrange from the left second lobe channel over a plurality of predetermined time periods. The predetermined time periods may overlap or may be non-overlapping.

In some embodiments, individual frequencies are compared and may be compared down to the nearest ten-thousandth of a hertz while the subranges are divided in 1 hertz bands up to 6 hertz bands. The aforementioned dividing points are used for illustrative purposes and changes in these points are within the scope of the invention. These ranges are contiguous but, also within the scope of the present invention is using subranges that are non-contiguous.

In some embodiments, the ranges are determined for each individual by looking for their dominant frequency range, which becomes a unique frequency subrange. Thus, the dominant frequency range may be the range when the person is most at rest, e.g., between 0.005 Hz and 48 Hz or between 16 and 23 Hertz. Alternatively, a system could use either of these as the subrange for one of both sets of corresponding lobes.

In order to determine whether asymmetries exist, the computer program product may be configured to calculate the energy from each subrange within each of a plurality of predetermined time periods for data from each channel and compare these energies to those measured from the same subrange of the corresponding lobe in the other hemisphere for the same time periods. Thus, one may calculate the average energy in a subrange. In order to do this, one may make use of digital signaling processors and band-pass filters. Additionally, the device may make use of Fast Fourier Transformation protocols to transform signals from time to frequency domains.

In some embodiments, the threshold difference of a subrange between hemispheres of a set of lobes is at least 3%, at least 10%, at least 20%, at least 30%, at least 40%, at least 50%, at least 60%, at least 70%, at least 80%, at least 90%, at least 100%, at least 150%, or at least 200% difference in energy over each of at least 5, at least 10, at least 20, at least 30, at least 40, at least 50, at least 60, at least 70, at least 80, or at least 100 consecutive time periods, wherein the time periods are 0.001 to 50 seconds or 5 to 30 seconds in length. In other embodiments, the threshold difference is at least 3%, at least 10%, at least 20%, at least 30%, at least 40%, at least 50%, at least 60%, at least 70%, at least 80%, at least 90%, at least 100%, at least 150%, or at least 200% difference in energy over at least 60%, at least 70%, at least 80% or at least 90% of at least 5, at least 10, at least 20, at least 30, at least 40, at least 50, at least 60, at least 70, at least 80, or at least 100 consecutive time periods, wherein the time periods are 0.001 to 50 seconds or 5 to 30 seconds in length.

In one embodiment, in order to determine if a lobe qualifies for rebalancing, the energy profile of each subrange of each channel is summarized over an epoch, which is a time period between 0.002 and 30 seconds. The most recently processed summaries may be stored in a revolving area of computer memory, e.g., the most recent 3-25 are processed and stored or the most recent 5-15 are processed and stored e.g., the most recent 5. These summaries may be stored on one or both of the devices and a remote data storage unit that is within or associated with or in communication with the central processing unit.

As each epoch is stored, the frequencies and subranges of the corresponding channels are compared to each other. These comparisons determine whether the threshold asymmetry has been crossed, and for example, the eligibility of corresponding lobes to initiate or to continue the balancing process.

By way of non-limiting examples, one may design the bounds of a mid-range based on eye-state (open vs. closed), age, or montage scalp placement of sensors or combinations thereof. Additionally, one can look for clusters of hemispheric frequency balances in a resting state for an individual or population and from there one may select a midrange (also referred to as a middle range). In some embodiments, the width of the midrange may be 4-18 hertz or 6-16 hertz or 8-14 hertz or 14-36 hertz. Further, in some embodiments the lower bound of the midrange may, for example, be 3.5 hertz, 4 hertz, 4.5 hertz, 5 hertz, 5.5 hertz, 6 hertz, 6.5 hertz, 7 hertz, 7.5 hertz, 8 hertz, 8.5 hertz, 9 hertz, 9.5 hertz, 10 hertz, 10.5 hertz, 11 hertz, 11.5 hertz, 12 hertz, 15 hertz, 18 hertz, or 20 hertz and the upper bound may be 12 hertz, 13 hertz, 14 hertz, 15 hertz, 18 hertz, 20 hertz, 22 hertz, 24 hertz, 26 hertz, 28 hertz, 30 hertz or 32 hertz.

Non-limiting examples of subranges appear in Table 1 below.

TABLE 1

| Example Number | First Subrange (Hz) | Second Subrange (Hz) | Third Subrange (Hz) |
| --- | --- | --- | --- |
| 1 | 0.125-10 | 10.1-25 | 25.1-48.50 |
| 2 | 0.125-15 | 15.1-20 | 20.1-48.50 |
| 3 | 1.0-8 | 12-30 | 30.1-45 |
| 4 | 2-12 | 15-19 | 32-40 |
| 5 | 0.125-12.5 | 12.6-22.4 | 22.5-48.50 |
| 6 | 0.125-.3.4 | 3.5-20 | 32.1-48.50 |
| 7 | 2.8 | 8.1-32 | 32.1-48.50 |

The Central Processing Unit

The central processing is configured to receive the measurements of electromagnetic activity from the device and to execute the asymmetry determination computer program product. The central processing unit may, for example, be located in a computer, which may, for example, be in the form of a tablet, a smart phone, a personal computer, or a networked computer.

In some embodiments, the computer is not connected to one or more other elements of the system through any wires. Thus, it is configured to communicate wirelessly with the device. In other embodiments, it is connected to a device (e.g., a housing the contains sensors, speakers and other hardware) of the present system through wires. In still other embodiments, the central processing unit may be within the same device. Furthermore, the central processing unit may be configured to execute computer program products automatically upon the receipt of instructions or data that may be used as input for the computer program product. Additionally, in some embodiments, a computer that houses the central processing unit comprises one or more of a graphic user interface, memory in the form of a data storage structure, an input device (e.g., a keyboard and/or mouse), a transmitter for transmitting information, and a receiver for receiving information. In some embodiments, the transmitter and/or receiver may be designed to send and to receive information that is communicated wirelessly through 3G, 4G, 5G, or Bluetooth technology or combinations thereof.

The central processing unit may be capable of generating a data message, wherein the data message contains information that indicates an observation of a material asymmetry in activity between one or both of: (i) the measurements from one or more subranges of the right first lobe channel and the measurements of corresponding subranges of the left first lobe channel; and (ii) the measurements from one or more subranges of the right second lobe channel and one or more subranges of the measurements from the left second lobe channel.

Optionally, the system further comprises a data storage unit, wherein the data storage unit is configured to store measurements of electromagnetic energy. In some embodiments, the data storage unit is located at or near the common location and is associated with a central processing unit. When there is a data storage unit, optionally the device has a USB port and/or a microUSB port and/or an HDMI port that allows for the transfer of data to a thumb drive or other portable data transfer structure that is capable of being inserted into a portal of a back-up computer.

In some embodiments, the system further comprises a transmitter. The transmitter may be located at or near the common location, and it may be capable of wirelessly or through wired connections, transmitting one or more data packages from the device processing unit to a central processing unit. The one or more data packages comprise information that corresponds to the measurement of electromagnetic energy. Each data package may comprise information from a single channel, information from a pair of channels for the same time period(s), or information from a plurality of pairs of channels for the same time periods(s).

In some embodiments, the system is portable and lacks wired connections to the central processing unit. In these embodiments, the components on or associated with a user's head communicate wirelessly with the central processing unit. In other embodiments, the elements, (which typically may be in a housing) are portable and are capable of communicating with the central processing unit either wirelessly or through wired connections that are removable. In other embodiments, the device is capable of communicating with the central processing unit only through wired connections.

Correlation Algorithms

Various embodiments make use of two correlation algorithms in order to determine what stimuli to deliver. These two algorithms may be part of the same computer program e.g., structured as modules within a computer program product, or they may be part of separate computer programs. After the asymmetry determination computer program product has determined that there is a threshold level of asymmetry, the two correlation algorithms are activated. The first correlation algorithm correlates each of a plurality of frequencies to a set of brain wave frequencies with an acoustic stimulus to form a variable sequence of acoustic stimuli. In some embodiments, the first correlation algorithm comprises, or is operably coupled to, a database and computer code instructions for retrieving information from the database. By way of a non-limiting example, in the database, dominant frequencies may be preassigned to sounds such as tone or musical notes or cords. These sounds may be assigned randomly or systematically, e.g., when using musical notes, higher frequencies may be associated with notes that are higher on a scale within the range of human hearing. Preferably, the acoustic stimuli are played in sequence to form a continuous mirror.

The variable sequence of acoustic stimuli is received by the speakers directly or indirectly from the central processing unit. In some embodiments, the variable sequence of acoustic stimuli is received in a plurality of data packets that is played in real time as they are received. As persons of ordinary skill in the art know, "real time" refers to the time that it takes to receive, to process, and to transmit data. For the human experience, this time may be negligible, e.g., milliseconds or shorter or longer. Furthermore, although the present disclosure refers to a sequence of sounds, because they are being generated and played in real time, the playback begins before the complete sequence has been generated.

In some embodiments, the variable sequence of acoustic stimuli is created only after the threshold asymmetry described above is detected. In other embodiments, as soon as a person begins transmitting brain signals a variable sequence of acoustic stimuli is played to support the balance of whichever corresponding lobe or set of lobes have the greater asymmetry in a subrange, regardless of whether it has crossed a threshold level is used.

The second correlation algorithm identifies electric stimulus to generate. As with the first correlation algorithm, it may comprise or be operably coupled to access a database to determine what electric stimulus to use to mirror brain activity. Accordingly, intermittently at regular or irregular intervals the second correlation algorithm will look to the dominant middle range frequency, and in real time, determine an electric stimuli that correlates to that frequency. It will then send instructions in e.g., data packets, to the necessary hardware to generate microvolt transcranial alternating electrical currents to the scalp at the appropriate locations. The system may be designed so that the first and second correlation algorithms use the same dominant middle range frequency in order to determine the stimuli to deliver for a given set of frequencies. However, these frequencies that are used by both algorithms will be a subset of what the first algorithm uses. Additionally, the second algorithms may be structured to search for the dominant frequency only intermittently and then transmit all of its results in real time or it may continuously search for the dominant frequencies, but only transmit results for predefined or random intermittent periods of time. In some embodiments, the first and second algorithms respond to input at the same time, e.g., 500 millisecond units or shorter and use the same dominant frequency to identify stimuli.

Optionally, each correlation algorithms may engage the 50 Hz and 60 Hz interference range to determine if interference is beyond a threshold. If the interference is unacceptable, the algorithms can modify or cause modification of the signal based on that interference in order to normalize the brain signals as if they contained an equal amount of interference within an acceptable interference range.

Playback Computer Program Product

The playback computer program product is stored in a tangible medium or in the cloud or on a network and is configured: (i) to be activated when there is material asymmetry in activity between the measurements from a subrange of frequencies of either the right first lobe channel and the left first lobe channel or the right second lobe channel and the left second lobe channel (and in some embodiments to be activated when there is no asymmetry but the device has nonetheless been activated or turned on for use); (ii) to apply the first correlation algorithm and the second correlation; and (iii) to control playing said acoustic stimuli through at least one speaker, and to deliver controlled frequency for microvolt electrical stimulation, through e.g., electrodes. Likewise, if coherence is too high, the correlation algorithm will quiet only one side or lobe allowing the brain to reset its own timing. The playback computer program product may be stored on the device or at a location other than on the device. The correlation algorithms may be distinct from the playback computer program product, e.g., separate files, or modules located within it or within a computer program product that contains both it and a module for the playback computer program.

Initiation and Switching

When data is collected from a plurality of lobes, then there may be the case that no threshold asymmetry is detected in either or any lobes. In these circumstances, the system may be designed to start with a particular default set of corresponding lobes and at regular intervals switch between sets of corresponding lobes until a threshold difference in energy is detected.

In some embodiments, when an imbalance is detected, the dominant frequency for identifying the sound is formulated or taken from the set of frequencies for the left and right sides of the lobes in which the imbalance was detected. The dominant brain wave frequency may, for example, be the dominant frequency between the subranges of the two lobes for which the threshold asymmetry was detected or an average of the dominant frequency between them. If during mirroring, the imbalance gets worse and it is in the high or low subranges, then the dominant frequency of the middle subrange may be taken exclusively from only one side of the pair of lobes and the electric stimulation be delivered to one side of a pair of lobes. The imbalance might be due to one side being much greater in amplitude than the other. In these cases, to address worsening imbalances, the methods may be designed to obtain dominant frequencies exclusively from the side that is less or least optimized and the stimulation frequency is delivered to that side.

In some embodiments, the method does not look for asymmetries prior to creating the initial variable sequence of acoustic stimuli. Instead, it looks for the greatest asymmetry regardless of threshold comparison or has a default setting for the lobe from which to begin creating the variable sequence of acoustic stimuli. After the initial time interval designated for stimulation, the stimulation frequency is delivered in the same manner as the acoustic and optionally, electric stimulation. As the system causes a variable sequence of acoustic and intermittent electric stimuli, it continues to monitor all channels, and upon a trigger event, for example a predetermined level or degree of change in asymmetry, is capable of dynamically switching to the middle range of another set of corresponding lobes channels as a source of dominant frequencies from which to generate the variable sequence of acoustic and electric stimuli.

Next, a variable sequence of acoustic stimuli is created by playing or combining each acoustic stimulus. The variable sequence of acoustic stimuli is played through a sound output device such as one or more speakers while at designated intervals the electric stimulation frequency is also delivered. The variable sequence of acoustic and electric stimuli is created to address an asymmetry in one set of lobes by playing or delivering frequency stimuli that are associated with dominant frequency or frequencies of the middle range from the same set of lobes in which the asymmetry was detected. Thus, by way of a non-limiting example, if in the frontal lobes, an asymmetry is detected in the first subrange that is greater than the threshold level, then the method will automatically look for the dominant frequencies in the middle range of the frontal lobes, activate the correlation algorithm to determine which stimulus corresponds to that frequency, and through the playback computer product and at the appropriate interval also through the electric stimulation, cause an output of that stimulus.

As the dominant frequency or frequencies change in the middle range, the stimuli to play will change and the variable sequence of acoustic stimuli will be developed along with intermittent electric stimuli to echo the brain. The variable sequence of acoustic stimuli is developed and played back in real time. Thus, for convenience of the reader, the variable sequence of acoustic stimuli is described as referring to the complete set of stimuli played back, but playback begins before the complete sequence is created. The variable sequence of acoustic stimuli may be played in both speakers or only in the speaker on one side of the head, e.g., the side for which the frequencies of the asymmetric subrange was larger or on the side for which the frequencies of the asymmetric subrange was smaller. The electric stimulation may also be delivered to sensors on one or both sides of the head in the same manner.

As the variable sequence of acoustic stimuli is being played back, each of the pairs of corresponding channels continues to be monitored. If the asymmetry is reduced to a subthreshold level or eradicated, the variable sequence of acoustic and electric stimuli may continue until the end of the user's session. In these circumstances, the middle range of the same set of corresponding lobes may be used for the source of the variable sequence of acoustic stimuli and electric stimuli until the end of the session; or if asymmetry is detected in the other corresponding set of lobes, the middle range of that set of lobes may be used as the source or the variable sequence of acoustic and electric stimuli; or if no asymmetry is detected in the other corresponding set of lobes, after a predetermined amount of time, the system may nonetheless switch to the other set of lobes as the source of the variable sequence of acoustic and electric stimuli.

When looking to threshold differences in energy, in some embodiments, the threshold difference in energy between energies measured is determined for each of a plurality of epochs, e.g., 5 to 100 or 10 to 50, wherein each epoch ranges from 0.5 to 30 seconds. Thus, the asymmetry must exist for at least a certain amount of time to be considered actionable.

In some embodiments, the measurements are made at a rate of at least 500 samples per second or at least 1000 samples per second. In some embodiments, 500 to 1000 samples per second are collected.

In some embodiments, the channels are configured to measure frequencies up to about 98.5 hertz.

By way of a non-limiting example, in some embodiments, brain signals are read (e.g., at 1 to 16 locations or at 1 to 4 locations, such as FP1/2 and T3/4; F3/F4 and P3/P4; C3/C4 and O1/2; AFZ/POZ and CB1/2). Algorithms compare the signals, determine where asymmetries, disproportional energy (frequencies on the spectral band), or inappropriate coherences exist.

Coherence

A coherence test may be for each epoch, and it may be in the form of a coherence qualification test for bi-hemisphere acoustic mirroring that is performed in each of the regions. Coherence is calculated as the square magnitude of the cross-spectral density of two signals divided by the product of their auto spectral densities at a given frequency.

$$\text{Coherence Function }(f) = \frac{[\text{Magnitude}(\text{Averaged } S_{AB}(f))]^2}{\text{Averaged } S_{AA}(f) \times \text{Averaged } S_{BB}(f)}$$

The result is a coherence value between zero and one for the signals of the two regions. A zero for the coherence value indicates no correlation between the two signals in terms of signal phase and amplitude. A value of one for the coherence indicates an exact match between the two signals (signal phase and amplitude). One method for calculating coherence is based on the MATLAB (matrix laboratory) mscohere function. This involves overlapping segments that are windowed, and the resulting windowed values being used to calculate the cross spectrum and power spectra.

Thus, to calculate the coherence, the signals are divided into overlapping segments that are then windowed. Fast Fourier Transforms (FFTs) are performed because cross-spectral and auto spectral densities are frequency domain values. The coherence is determined by averaging the coherence value from each segment. Thus, the asymmetry determination computer program products may be configured to determine whether or one or both of a threshold level of asymmetry and/or a threshold level of lack of coherence exists during rebalancing.

Dynamic Monitoring and Rebalancing

As persons of ordinary skill in the art will recognize, the brain is constantly active. Therefore, even if asymmetries are detected in one pair of lobes, the brain may at the same time or at other times, have asymmetry in other lobes.

In some embodiments, a threshold difference is detected between measurements from channels of both the first pair of corresponding lobe channels and the second pair of corresponding lobe channels. In these cases, the dominant brain wave frequencies may be selected from the second subrange of frequencies of the lobes for which a subrange had the greater asymmetry or a user may select which lobe he or she would prefer to balance first and then when balance is below the threshold level, the system may automatically switch to the other lobes.

In some embodiments, the asymmetry is detected from between corresponding subranges of the first lobe, and the dominant frequency from which the variable sequence of acoustic stimuli and variable intermittent electric stimuli are generated is from a middle subrange of the first set of corresponding lobes. The method may further comprise continuing to search for asymmetries during playing of the variable sequence of acoustic stimuli and delivery of the frequency for electric stimulus, and if greater asymmetry is detected in another set of lobes, e.g., a switching threshold asymmetry in energies is detected from at least one of the corresponding subranges measured from the second corresponding lobes, then the method further comprises creating a new variable sequence of acoustic and electric stimuli, wherein the new variable sequence of acoustic and electric stimuli comprises stimuli for each of a set of dominant frequencies from the second pair of lobes; and playing the new variable sequence of acoustic stimuli as well as delivery of the appropriate electric stimuli. If the asymmetry is from a different subrange of the same corresponding lobes, then one would continue with generating the variable sequence of acoustic and electric stimuli from the dominant frequency of the second or middle subrange of those lobes. In some embodiments, a switching threshold is an asymmetry that is either a threshold asymmetry as described above provided that it is greater than the greatest asymmetry in the other corresponding set of lobes or is at least 3%, at least 5%, at least 10%, at least 20%, at least 40%, at least 60%, or at least 80% greater than the greatest asymmetry in the other corresponding set of lobes.

In some embodiments, the asymmetry is detected from between corresponding subranges of the second corresponding lobes and the dominant frequency from which the variable sequence of acoustic stimuli and variable intermittent electric stimuli is generated is also from the second pair of lobes. The method may further comprise continuing to search for asymmetries during playing of the variable sequence of acoustic stimuli and delivery of electric stimuli, and if greater asymmetry is detected in another lobe, e.g., a switching threshold asymmetry in energies is detected from at least one of the corresponding subranges measured from the first pair of lobes, then the method further comprises creating a new variable sequence of acoustic stimuli and variable intermittent electric stimuli, wherein the new variable sequence of acoustic and electric stimuli comprises an acoustic and electric stimulus for each of a set of dominant frequencies from the first lobes; and playing the new variable sequence of acoustic stimuli and delivering the electric stimulus.

In some embodiments, one may simultaneously analyze coherence in each of the frequency ranges of two, three, or four corresponding sets of lobes of the brain, and if there is insufficient coherence in any pair of lobes, these may be triaged in order of degree of lack of coherence and addressed in that order. When addressing a lack of coherence one may, e.g., redefine the middle subrange to generate a different variable sequence of acoustic and electric stimuli.

Dynamic rebalancing may occur after there has been a trigger event. A trigger event may be a predetermined increase in a difference in energy between energies measured within any one or more of a single frequency, a first subrange of frequencies, a second subrange of frequencies, and up to the last subrange of frequencies of corresponding lobe channels from which either the dominant frequency was measured or the dominant frequency was not measured. Alternatively or additionally, the trigger event is a predetermined decrease in a difference in energy between energies measured within any one or more of a single frequency, a first subrange of frequencies, a second subrange of frequencies, and a last subrange of frequencies of corresponding lobe channels from which either the dominant frequency was measured or the dominant frequency was not measured. The predetermined increase or decrease may be an absolute number or a percentage, e.g., at least 2%, at least 5%, at least 10%, at least 20% or at least 30%.

Hardware

Figure 2:
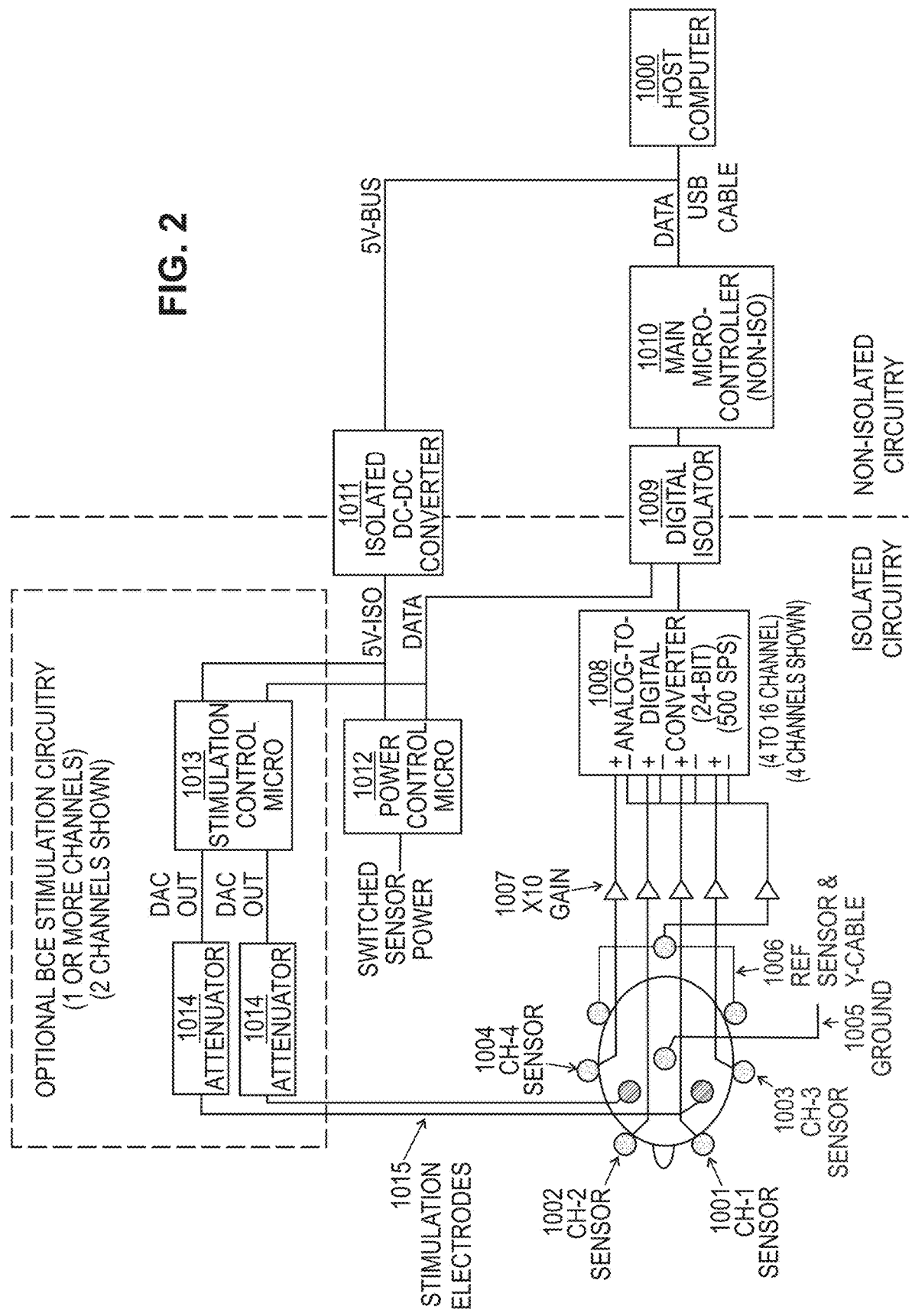
FIG. 2 is a representation of circuitry of a system of the present invention.

In some embodiments, the systems of the present invention contain all of the electronics for acquiring data, including cabled sensors, stimulation electrodes, speakers, EEG amplifier/stimulation unit, and USB cable for connection to a host computer. Optionally, they may all be part of a single device or form a system. An example of a configuration of the hardware that may be used on or in connection with a device is illustrated by reference to FIG. 2.

Electrical Design

The system as shown accommodates reading four to sixteen channels of sensor data, depending on model of the amplifier. The system's ADC (Analog-to-Digital-Converter) 1008 may, for example, be an ADS1294 chip from Texas Instruments that provides four channels of data. The channels are simultaneously-acquired at a 500-sample-per-second rate, providing a frequency spectrum resolvable up to almost 250 Hz. In a 24-bit ADC, there is a theoretical amplitude resolution of 145 dB (decibels). This system yields over 120 dB dynamic range with ADC inputs shorted, and typically over 90 dB dynamic range with-respect-to the sensor inputs. The result is an EEG system that: (i) needs no adjustable gain ranging amplifiers; and (ii) has vast headroom that allows power line(s) and other common-mode signals to coexist (and subsequently be removed from the desired differential signal) without signal clipping issues, and a very low noise floor. A noise floor is how far down a signal can be read without being washed out by noise. Clipping is flattening of a signal above/below an upper range for the positive/negative amplitude of a signal where nothing is read due to excessive noise interference above the upper +/−amplitude limit.

Information collected by the four sensor channels (with-respect-to the reference channel on the ear sensor Y-cable 1006), 1001 (Channel-1 sensor), 1002 (Channel-2 sensor), 1003 (Channel-3 sensor) and 1004 (Channel-4 sensor) are digitized from the active cabled sensors affixed to the head, and sent over a USB data cable to the host computer 1000. The ear reference is a standard sensor cable with addition of a Y-cable that connects both ears together to the sensor for a symmetrical reference signal. Electric potential is determined as it exists as a difference between two points. The active sensors have a standard reference (the ears), which is approximately zero brain signal and generally also has the same common-mode interference as the active sensors. Therefore, Actual potential=(Active−Reference)

for each separate active sensor and the common-mode interference recorded in both the active and the reference sensors then cancel each other out. The ear sensor is depicted as the reference point, but in other embodiments, one may use a dynamic reference in order to find the difference between any two points.

The cabled head sensors use active CMOS buffers with Schottky diodes to clamp transient events such as static discharge, driving the buffered signal over a shielded cable from each head sensor to the amplifier. The sensor and reference signals are applied to input preamplifiers 1007, which provide gain and signal conditioning prior to the ADC.

An EEG system is comprised of a number of sensors that are placed at specific locations on the scalp. A "reference" sensor is split via a Y-cable and clipped onto both earlobes; the ears are electrically-quiet locations on the head. The signals of interest are measured differentially: sensor with-respect-to reference. The signals of interest are in the microvolt range, but they are summed with larger "common-mode" signals that exist in unison on the reference and sensor signals. The differential measurement removes most of the common-mode signal.

The human body acts as an antenna capacitively-coupled to earth ground, and immersed in the electromagnetic fields of surrounding AC power lines and other noise sources. The largest contribution is from the 50-Hz or 60-Hz power system. The body will have a certain potential with respect to earth ground, and the EEG amplifier system, which is also capacitively-coupled to earth ground, will likely have a different potential with respect to Earth ground. When the amplifier sensors are connected to the body, the difference between the body and amplifier potentials (due to capacitive coupling of each) results in potentials of 50-Hz or 60-Hz and other noise being added as common-mode signals to the reference and sensor amplifier inputs, which is generally in levels far in excess of the amplifier's allowable common-mode range.

An additional EEG system connection to the body is a "ground" electrode 1005, which is utilized to minimize these large common-mode signals. Ground is the point of zero potential in the amplifier circuitry, and when connected to the body, shorts-out the body and amplifier capacitive-coupling paths to earth ground, thereby eliminating much of the common mode signal. The ground connection may be located at any convenient point on the body but is typically attached to a location on the top center of the head.

Isolation is provided to separate the host computer USB connection from the circuitry connected to the subject's head. The 5V bus voltage from the host USB cable connects to a DC-DC Converter 1011, which provides an isolated voltage source to power the isolated section. The data stream from the ADC and control data connects through a digital isolator 1009. Data streaming and system control is provided by the main microcontroller 1010 in the non-isolated section. A power control microcontroller 1012 in the isolated section switches power to the cabled sensors for operation, and disables the sensors in the standby state.

Optional Cereset-e Stimulation Module

The optional Cereset-e Stimulation Module plugs onto the main amplifier circuit board, connecting to isolated power and control ports. In other embodiments, this circuitry may be combined on the amplifier circuit board. A stimulation control microcontroller 1013 provides one or more channels of sinusoidal stimulus frequencies via digital-to-analog converters (DAC), as commanded by the host computer. The DAC outputs are attenuated to desired stimulation amplitudes 1014 and connect to the stimulation electrodes 1015.

FIG. 1 provides a flowchart that is an overview of the present invention. The method starts with obtaining input signals from one to sixteen channels 100. Next, the system composes, displays, stores frequency symmetry, and determines coherence and proportionation 200. Data is sent to a memory device to be stored by channel, frequency, and episode 300. Additionally, when the system compares data 200, if the data is outside of certain parameters, it will correlate a dominant mid-range frequency using a single channel 600. If the data is within certain parameters, it will correlate the dominant mid-range frequency from a plurality of channels 700.

Following the comparison and storage of data, the system will: (1) deliver frequency based electric stimulation at determined time intervals 400; and (2) play sound in pitch and rhythm 800.

Various aspects of the present invention have been described for use in connection with one or more embodiments. However, unless explicitly stated or otherwise apparent from context, each feature described above in any one embodiment may be used in connection with any and all embodiments.

We claim:

1. A method for decreasing brain asymmetry comprising:
   (a) simultaneously measuring electromagnetic activity of a user's brain through a set of channels, wherein the set of channels comprises
      (i) a first pair of corresponding lobe channels, wherein the first pair of corresponding lobe channels is comprised of a right first lobe channel and a left first lobe channel, and
      (ii) a second pair of corresponding lobe channels, wherein the second pair of corresponding lobe channels is comprised of a right second lobe channel and a left second lobe channel,
   wherein each channel is configured to measure electromagnetic energy in a region of a brain of a user and to generate a measurement of electromagnetic energy and wherein the first pair of corresponding lobe channels is configured to measure electromagnetic energy from corresponding left-right regions of a first lobe and the second pair of corresponding lobe channels is configured to measure electromagnetic energy from corresponding left-right regions of a second lobe, wherein the first lobe is not the same as the second lobe;
   (b) determining whether there is a threshold difference in energy between energies measured for any single frequency or for any one or more ranges of frequencies as measured between each channel of each pair of corresponding lobe channels,
   (c) when there is a determination of a threshold difference in energy,
      (i) activating a first correlation algorithm, wherein for each of a first plurality of frequencies from a set of dominant middle range brain wave frequencies from a lobe for which there has been a determination of a threshold difference in energy, the first correlation algorithm identifies an acoustic stimulus, and
      (ii) activating a second correlation algorithm, wherein for each of a second plurality of frequencies from the set of dominant middle range brain wave frequencies from the lobe for which there has been a determination of a threshold difference in energy, intermittently the second correlation algorithm identifies an electric stimulus, wherein the second plurality of frequencies is a subset of the first plurality of frequencies,
   (d) creating a variable sequence of acoustic stimuli by combining each acoustic stimulus identified in (c)(i) and playing said variable sequence of acoustic stimuli through a sound output device, and
   (e) delivering to the user each electric stimulus identified in (c)(ii), wherein when each electric stimulus is delivered to the user, an acoustic stimulus that correlates with the same dominant middle range brain wave frequency is simultaneously delivered.

2. The method according to claim 1, wherein the asymmetry determination computer program product is stored in a tangible medium and when applied determines whether there is a threshold difference in energy between energies measured within any one or more of a single frequency, a first subrange of frequencies, a second subrange of frequencies, and a third subrange of frequencies.

3. The method according to claim 2, wherein the asymmetry determination computer program product is configured to determine whether there is a threshold difference in energy by comparing a calculated energy of the frequencies within a plurality of subranges from the right first lobe channels with a calculated energy of the frequencies of a plurality of subranges from the left first lobe channels over a plurality of predetermined time periods.

4. The method according to claim 1, wherein the sound output device is configured to rest on a user's head or is housed in a device that rests on a user's head.

5. The method according to claim 1, wherein each electric stimulus is in the form of a microvolt transcranial alternating current stimulation.

6. The method according to claim 1, wherein the asymmetry determination computer program product is further configured to dynamically switch the lobes from which the asymmetry determination computer program product obtains the dominant frequencies upon occurrence of a trigger event.

7. The method according to claim 1, wherein the threshold difference in energy between energies measured is determined for each of a plurality of epochs, wherein each epoch ranges from 0.5 to 30 seconds.

8. The method according to claim 7, wherein said measurements are made at a rate of at least 500 samples per second.

9. The method according to claim 1, wherein the channels are configured to measure frequencies up to about 100 hertz.

10. A method for changing brain activity comprising:
(a) simultaneously measuring electromagnetic activity of a user's brain through a set of channels, wherein the set of channels comprises
    (i.) a first pair of channels, wherein the first pair of channels is comprised of a right first lobe channel and a right second lobe channel, wherein the right first lobe channel is configured to measure electromagnetic energy in a first lobe in a first hemisphere of a brain of a user and the right second lobe channel is configured to measure electromagnetic energy in a second lobe in the first hemisphere of the brain of the user, and
    (ii.) a second pair of channels, wherein the second pair of channels is comprised of a left first lobe channel and a left second lobe channel, wherein the left first lobe channel is configured to measure electromagnetic energy in the first lobe in a second hemisphere of a brain of a user and the right second lobe channel is configured to measure electromagnetic energy in the second lobe in the second hemisphere of the brain of the user,
wherein each channel is configured to generate a measurement of electromagnetic energy, wherein the first hemisphere is not the same as the second hemisphere;
(b) determining whether there is a threshold difference in energy between energies measured for any single frequency or for any one or more ranges of frequencies as measured between each channel of each pair of channels,
(c) when there is a determination of a threshold difference in energy,
    (i.) activating a first correlation algorithm, wherein for each of a first plurality of frequencies from a set of dominant middle range brain wave frequencies from a hemisphere for which there has been a determination of a threshold difference in energy, the first correlation algorithm identifies an acoustic stimulus, and
    (ii.) activating a second correlation algorithm, wherein for each of a second plurality of frequencies from the set of dominant middle range brain wave frequencies from the hemisphere for which there has been a determination of a threshold difference in energy, intermittently the second correlation algorithm identifies an electric stimulus, wherein the second plurality of frequencies is a subset of the first plurality of frequencies,
(d) creating a variable sequence of acoustic stimuli by combining each acoustic stimulus identified in (c)(i) and playing said variable sequence of acoustic stimuli through a sound output device, and
(e) delivering to the user each electric stimulus identified in (c)(ii), wherein when each electric stimulus is delivered to the user, an acoustic stimulus that correlates with the same dominant middle range brain wave frequency is simultaneously delivered.

11. The method according to claim 10, wherein the asymmetry determination computer program product is stored in a tangible medium and when applied determines whether there is a threshold difference in energy between energies measured within any one or more of a single frequency, a first subrange of frequencies, a second subrange of frequencies, and a third subrange of frequencies.

12. The method according to claim 11, wherein the asymmetry determination computer program product is configured to determine whether there is a threshold difference in energy by comparing a calculated energy of the frequencies within a plurality of subranges from the right first lobe channels with a calculated energy of the frequencies of a plurality of subranges from the left first lobe channels over a plurality of predetermined time periods.

13. The method according to claim 10, wherein the sound output device is configured to rest on a user's head or is housed in a device that rests on a user's head.

14. The method according to claim 10, wherein each electric stimulus is in the form of a microvolt transcranial alternating current stimulation.

15. The method according to claim 10, wherein the asymmetry determination computer program product is further configured to dynamically switch the lobes from which the asymmetry determination computer program product obtains the dominant frequencies upon occurrence of a trigger event.

16. The method according to claim 10, wherein the threshold difference in energy between energies measured is determined for each of a plurality of epochs, wherein each epoch ranges from 0.5 to 30 seconds.

17. The method according to claim 16, wherein said measurements are made at a rate of at least 500 samples per second.

18. The method according to claim 10, wherein the channels are configured to measure frequencies up to about 100 hertz.

* * * * *